US006440741B2

(12) United States Patent
Fisher et al.

(10) Patent No.: US 6,440,741 B2
(45) Date of Patent: *Aug. 27, 2002

(54) EXPRESSION VECTOR FOR CONSISTENT CELLULAR EXPRESSION OF THE TET ON REPRESSOR IN MULTIPLE CELL TYPES

(75) Inventors: Paul B. Fisher, Scarsdale; Rahul Gopalkrishnan, New York, both of NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/268,303

(22) Filed: Mar. 15, 1999

(51) Int. Cl.[7] .................. C12N 15/00; C12N 15/63; C12N 5/00; C12P 21/06

(52) U.S. Cl. .................. 435/455; 435/320.1; 435/325; 435/69.1

(58) Field of Search .................. 435/320.1, 375, 435/69.1, 455

(56) References Cited

U.S. PATENT DOCUMENTS 5,464,758 A    11/1995  Gossen et al. .............. 435/69.1
5,654,168 A  *  8/1997  Bujard et al. .............. 435/69.1

OTHER PUBLICATIONS

Goldman et al., BioTechniques, vol. 21 (6), p. 1013–1015, 1996.*
Palmiter et al., Science 222: 809–814, Nov. 1983.*
Pursel et al., J. Reprod. Fert., Suppl. 40, p. 235–245, 1990.*
Kappel et al., Current Opinion in Biotechnology, 3: 548–553, 1992.*
Gossen et al., Science, 268: 1766–1769, Jun. 1995.*
Ackland–Berglund, C.E., and Leib, D.A., (1995) The Efficacy of Tetracyline–Controlled Gene Expression is Influenced by Cell Type *Bio. Techniques*, 18:196–200 (Exhibit 1).
Blau, H., and Rossi, F.M.V., (1999) "Tet B or not B: Advances in tetracycline–inducible gene expression" *Proc. Natl. Acad. Sci. USA*, 96:797–799 (Exhibit 2).
Gossen, M., Bonin, A.1., Freudlieb, S., and Bujard, H., (1994) "Inducible gene expression systems for higher eukaryotic cells" *Curr. Opin. Biotechnol*, 5:516–520 (Exhibit 3).
Gossen, M., and Bujard, H., (1995) "Efficacy of tertracycline–controlled gene expression influenced by cell type: commentary" *Biotechniques*, 19:213–216 (Exhibit 4).
Gossen, M., and Bujard, H., (1992) "Tight control of gene expression in mammalian cells by tetracycline–responsive promoters" *Proc. Natl. Acad. Sci. USA*, 89:5547–5551 (Exhibit 5).

(List continued on next page.)

*Primary Examiner*—Scott D. Priebe
*Assistant Examiner*—Shin-Lin Chen

(57) ABSTRACT

A vector having the Protein Translation Peptide Elongation Factor-1α (EF-1α) promoter and nucleic acids encoding a reverse tetracycline-controlled activator is provided, wherein the expression of the activator is under the control of the EF-1α promoter. In addition, a method of generating a reverse tetracycline-controlled transactivator expression system for inducible tetracycline-regulated gene expression is provided that consists of: (a) isolation of a DNA fragment encoding the reverse tetracycline-controlled transactivator, (b) isolation of a DNA fragment containing the EF-1α promoter, (c) subcloning of these DNA fragments into a plasmid or other suitable vector to create a vector in which the reverse tetracycline-controlled transactivator is operably linked to the EF-1α promoter.

8 Claims, 5 Drawing Sheets

OTHER PUBLICATIONS

Gossen, M., Freundlieb, S., Bender, G., Muller, G., Hillen, W., and Bujard, H., (1995) "Transcriptional activation by tetracyclines in mammalian cells" *Sci.*, 268:1766–1769 (Exhibit 6).

Liang, X., Hartikka, J., Sukhu, L., Manthrope, M., and Hobart, P., (1996) "Novel, high expressing and antibiotic-controlled plasmid vectors designed for use in gene therapy" *Gene Tehr.*, 3:350–356 (Exhibit 7); and.

Shockett, P.E., and Schartz, D.G., (1996) "Diverse strategies for tetracycline–regulated inducble gene expression" *Proc. Natl. Acd. Sci. USA*, 93:5173–5176 (Exhibit 8).

Akagi, K., Kanai, M., Saya, H., Kozu, T., and Berns, A. (2001). A novel tetracycline–dependent transactivator with E2F4 transcriptional activation domain. *Nucleic Acids Res.* 29:e23.

Gopalkrishnan, R.V., Christiansen, K.A., Goldstein, N.I., DePinho, R.A., and Fisher, P.B. (1999). Use of the human EF–1alpha promoter for expression can significantly increase success in establishing stable cell lines with consistent expression: a study using the tetracycline–inducible system in human cancer cells.

Strathdee, C.A., McLeod, M.R., and Hall, J.R. (1999). Efficient control of tetracycline–responsive gene expression from an autoregulated bi–directional expression vector. *Gene* 229:21–29.

Bieschke, E.E., Wheeler, J.C., and Tower, J. (1998). Doxycycline–induced transgene expression during Drosophilia development and aging. *Mol. Gen. Genet.* 258:571–579.

Gallia, G.L., and Khalili, K. (1998). Evaluation of an autoregulatory tetracycline regulated system. *Oncogene* 16:1879–1884.

Kang, D.C., Motwani, M., and Fisher, P.B. (1998). Role of the transcription factor AP–1 in melanoma differentiation (review). *Int. J. Oncol.* 13:1117–1126.

Kringstein, A.M., Rossi, F.M., Hofmann, A., and Blau, H.M. (1998). Graded transcriptional response to different concentrations of a single trasactivator. *Proc. Natl. Acad. Sci. USA* 95:13670–13675.

Rossi, F.M., Guicherit, O.M., Spicher, A., Kringstein, A.M., Fatyol, K., Blakely, B.T., and Blau, H.M. (1998). Tetracycline–regulatable factors with distinct dimerization domains allow reversible growth inhibition by p16. *Nat. Genet.* 20:389–393.

Bohl, D., Naffakh, N., and Heard, J.M. (1997). Long–term control of erythoropoietein secretion by doxycycline in mice transplanted with engineered primary myoblasts. *Nat. Med.* 3:299–305.

Efrat, S., Fusco–DeMane, D., Lemberg, H., al Emran, O., and Wang, X. (1995). Conditional transformation of a pancreatic beta–cell line derived from transgenic mice expressing a tetracycline–regulated oncogene. *Proc. Natl. Acad. Sci USA* 92:3576–3580.

Hennighausen, L., Wall, R.J., Tillmann, U.M., and; Furth, P.A. (1995). Conditional gene expression in secretory tissues and skin of transgenic mice using the MMTV–LTR and the tetracycline responsive system. *J. Cell. Biochem.* 59:463–472.

Miller, K., and Rizzino, A. (1995). The function of inducible promoter systems in F9 embryonal carcinoma cells. *Exp. Cell Res.* 218:144–150.

Shockett, P., Difilippantonio, M., Hellman, N., and Schatz, D.G. (1995). A modified tetracycline–regulated inducible gene expression. *Proc. Natl. Acad. Sci. USA* 92:6522–6566.

Fishman, G. I., Kaplan, M.L., and Buttrick, P.M. (1994). Tetracycline–regulated cardiac gene expression in vivo. *J. Clin. Invest.* 93:1864–1868.

Furth, P.A., St. Onge, L., Boger, H., Gruss, P., Gossen, M., Kistner, A., Bujard, H., and Hennighausen, L. (1994). Temporal control of gene expression in transgenic mice by a tetracycline–responsive promoter. *Proc. Natl. Acad. Sci USA* 91:9302–9306.

Wakabayashi–Ito, N., and Nagata, S. (1994). Characterization of the regulatory elements in the promoter of the human elongation factor–1 alpha gene. *J. Biol. Chem.* 269:29831–29837.

Weinmann, P., Gossen, M., Hillen, W., Bujard, H., and Gatz, C. (1994). A chimeric transactivator allows tetracycline–responsive gene expression in whole plants. *Plant J.* 5:559–569.

Kappel C.A., Zhang S.X., Bieberich C.J., and Jay G. (1992). Regulating gene expression in transgenic animals. *Curr. Opin. Biotechnol.* 3:548–553.

Li, M., Hantzopoulos, P.A., Banerjee, D., Zhao, S.C., Schweitzer, B.I., Gilboa, E., and Bertino, J.R. (1992). Comparison of the expression of a mutant dihydrofolate reductase under control of different internal promoters in retroviral vectors. *Hum. Gene Ther.* 3:381–390.

McKnight, R.A., Shamay, A., Sankaran, L., Wall, R.J., and Hennighausen, L. (1992). Matrix–attachment regions can impart position–indendent regulation of a tissue– specific gene in transgenic mice. *Proc. Natl. Acad. Sci. USA* 89:6943–6947.

Hasegawa, T., Nakada, S., Nakajima, T., Oda, K., Kawata, M., Kimura, H., and Sekiya, S. (1990). Expression of various viral and cellular enhancer–promoters during differentiation of human embryonal carcinoma cells. *Differentiation* 42:191–198.

Kim, D.W., Uetsuki, T., Kaziro, Y., Yamaguchi, N., and Sugano, S. (1990). Uses of the human elongation factor 1 alpha promoter as a versatile and efficient expression system. *Gene* 91:217–223.

Pursel V.G., Bolt D.J., Miller K.F., Pinkert C.A., Hammer R.E., Palmiter R.D., and Brinster R.L. (1990). Expression and performance in transgenic pigs. *J. Reprod. Fertil. Suppl.* 40:235–245.

Stief, A., Winter, D.M., Stratling, W.H., and Sippel, A.E. (1989). A nuclear DNA attachment element mediates elevated and position–independent gene activity. *Nature* 341:343–345.

Sleigh, M. J. (1987). Differential regulation of viral and cellular genes in F9 mouse embryonal carcinoma cells. *Nucleic Acids Res.* 15:9379–9395.

Gorman, C.M., Rigby, P.W., and Lane, D. P. (1985). Negative regulation of viral enhancers in undifferentiated embryonic stem cells. *Cell* 42:519–526.

Palmiter R.D., Norstedt G., Gelinas R.E., Hammer R.E., and Brinster R.L. (1983). Metallothionein–human GH fusion genes stimulate growth of mice. *Science* 222:809–814.

Faiss, M., Zalubilova, J., Strnad, M., and Schmulling, T. (1997). Conditional transgenic expression of the ipt gene indicates a function for cytokinins in paracrine signaling in whole tobacco plants. *Plant J.* 12:401–415

Fussenegger, M., Moser, S., Mazur, X., and Bailey, J.E. (1997). Autoregulated multicistronic expression vectors provide one–step cloning of regulated product gene expression in mammalian cells. *Biotechnol Prog.* 13:733–740.

Hoffmann, A., Villalba, M., Journot, L., and Spengler, D. (1997). A novel tetracycline–dependent expression vector with low basal expression and potent regulatory properties in various mammalian cell lines. *Nucleic Acids Res.* 25:1078–1079.

Holwell, T.A., Schweitzer, S.C., and Evans, R.M. (1997). Tetracycline regulated expression of vimentin in fibroblasts derived from vimentin null mice. *J. Cell. Sci.* 110:1947–1957.

Jost, M., Kari, C., and Rodeck, U. (1997). An episomal vector for stable tetracycline–regulated gene expression. *Nucleic Acids Res.* 25:3131–3134.

Qin, L., Ding, Y., Pahud, D.R., Chang, E., Imperiale, M.J., Bromberg, J.S. (1997). Promoter attenuation in gene therapy: interferon–gamma and tumor necrosis factor–alpha inhibit transgene expression. *Hum. Gene Ther.* 8:2019–29.

Thompson, A.J., and Myatt, S.C. (1997). Tetracycline–dependent activation of an upstream promoter reveals transcriptional interference between tandem genes within T–DNA in tomato. *Plant Mol. Biol.* 34:687–692.

Hofmann, A., Nolan, G.P., and Blau, H.M. (1996). Rapid retroviral delivery of tetracycline–inducible genes in a single autoregulatory cassette. *Proc. Natl. Acad. Sci. USA* 93:5185–5190.

Jiang, H., Su, Z.Z., Lin, J.J., Goldstein, N.I., Young, C.S., and Fisher, P.B. (1996). The melanoma differentiation associated gene mda–7 suppresses cancer cell growth. *Proc. Natl. Acad. Sci. USA* 93:9160–9165.

Paulus, W., Baur, I., Boyce, F.M., Breakefield, X.O., and Reeves, S.A., (1996). Self–contained, tetracycline–regulated retroviral vector system for gene delivery to mammalian cells. *J. Virol.* 70:62–67.

Schultze, N., Burki, Y., Lang, Y., Certa, U., and Bluethmann, H. (1996). Efficient control of gene expression by single step integration of the tetracycline system in transgenic mice. *Nat. Biotechnol.* 14:499–503.

Baron, U., Ferundlieb, S., Gossen, M., and Bujard, H. (1995). Co–regulation of two gene activities by tetracycline via a bidirectional promoter. *Nucleic Acids Res.* 23:3605–3606.

Dhawan, J., Rando, T.A., Elson, S.L., Bujard, H., and Blau, H.M. (1995). Tetracycline–regulated gene expression following direct gene transfer into mouse skeletal muscle. *Somat. Cell. Mol. Genet.* 21:233–240.

* cited by examiner

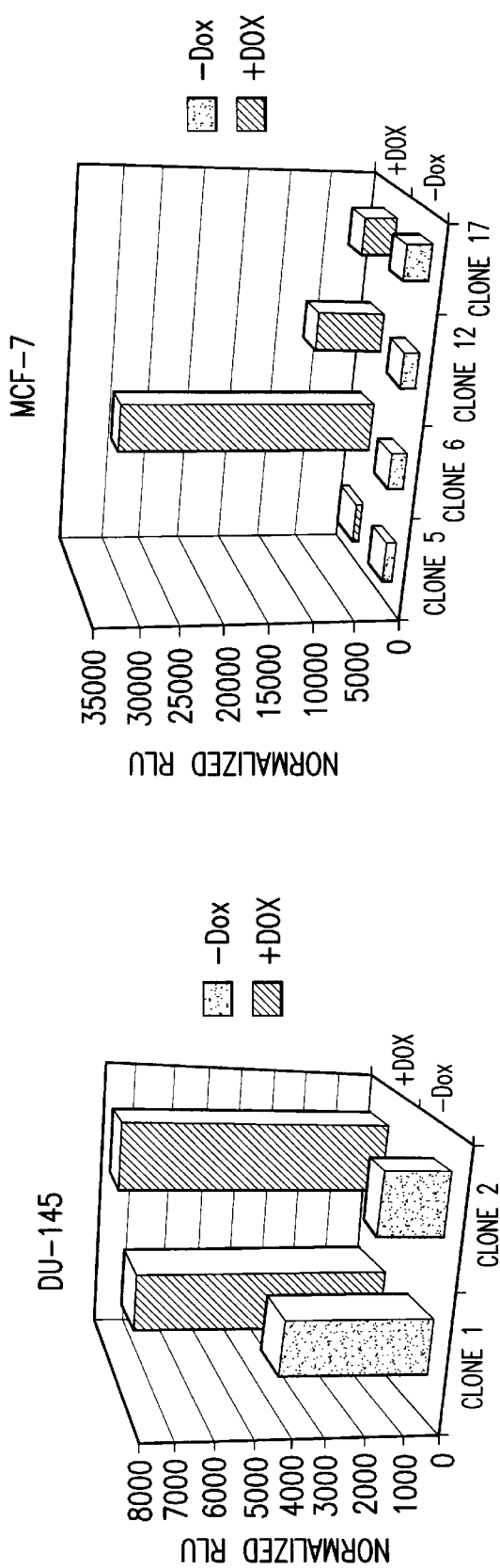
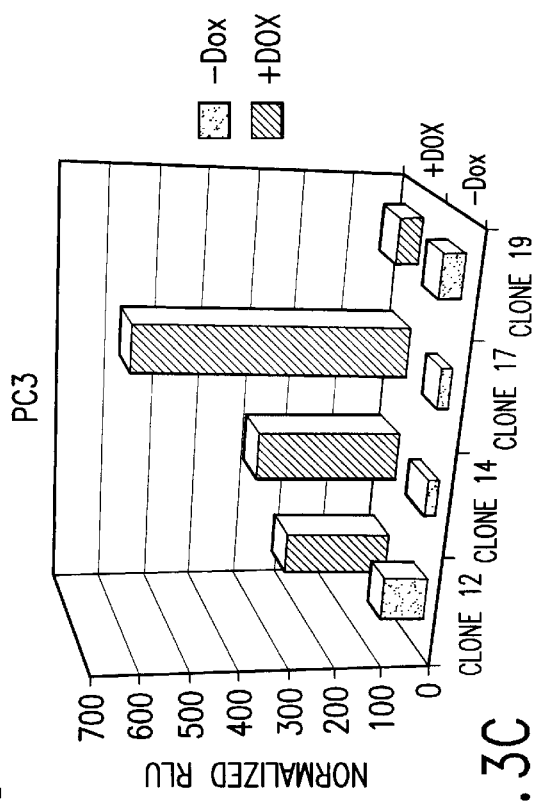
FIG. 3A
FIG. 3B
FIG. 3C

EXPRESSION VECTOR FOR CONSISTENT CELLULAR EXPRESSION OF THE TET ON REPRESSOR IN MULTIPLE CELL TYPES

The invention disclosed herein was made with Government support under Grant No. CA 35675 from the National Institutes of Health, U.S. Department of Health and Human Services. Accordingly, the U.S. Government has certain rights in this invention.

Throughout this application, various publications are referenced. The disclosures of these publications in their entireties are hereby incorporated by reference in order to more fully describe the state of the art as known to those skilled therein as of the date of the invention described and claimed herein.

BACKGROUND OF THE INVENTION

Since the first report by Gossen and Bujard (Gossen and Bujard, 1992) and subsequent documentation of a variant form (Gossen et al., 1995), the Tetracycline (Tc)-regulated system, has been broadly adopted and is widely acknowledged as the method of choice, in experiments requiring inducible expression of genes of interest. In its originally reported form, the system employs two plasmids. One expressing the tTA or rtTA cDNA (henceforth jointly referred to as TA), a fusion protein of the bacterial Tc-repressor, fused to the C-terminal acidic activation domain of the Herpes Simplex virus (HSV), VP16 transcriptional transactivator. The second plasmid enables cloning of a cDNA of interest downstream of a heptamerized Tc-operator transcription regulatory DNA sequence, fused to a DNA element providing basal promoter activity, derived either from the CMV IE or HSV thymidine kinase promoters Establishing a cell line having Tc-regulatable expression of the gene of interest involves a two step process. In the first, a cell line stably expressing the TA cDNA is established and identified by clonal selection and expression analysis through transient transfection with a Tc-responsive reporter. In the second step, the gene of interest cloned under control of the Tc-responsive element is introduced into the cell line made in the previous step and a second round of selection is performed to identify clones displaying Tc-responsive inducibility of the cDNA (Gossen and Bujard, 1992; Gossen et al., 1995). The Tc-regulated system has effectively overcome several drawbacks seen in earlier systems which showed high basal levels of expression, poor responsiveness and toxicity of the inducing agent. The Tc-inducible system is in addition, able to achieve induction over ranges of several orders of magnitude in a graded manner, responsive to varying levels of inducer. Furthermore, the system is extremely versatile and amenable to several types of modifications, permitting the study of the role of a particular gene, or combinations thereof, in a wide variety of cell types of interest. The potential to use this system in medical applications including gene therapy protocols and pharmacological small molecule screening are areas of active investigation. Its versatility has enabled adaptation to situations requiring inducible gene expression in a tissue specific or generalized manner in animal or plant models, opening new avenues to study gene function in vivo.

The Tc-inducible expression system has been modified in several ways, in attempts to improve performance or tailor it to specific needs. Autoregulatory control was achieved by placing both the tTA as well as exogenous cDNA under control of Tc-operator sequences (Shocket et al., 1995), which reportedly permitted regulation of available tTA levels only on induction and thereby increased overall performance in terms of inducibility and frequency of positive clones obtained. Single plasmid vectors containing the tTA sequence and gene of interest in opposite orientations have been developed to obviate the need for multiple rounds of clonal selection (Baron et al., 1995; Schultze et al., 1996; Weinmann et al., 1994). Overcoming a sometimes considerable barrier of introduction of DNA into transfection recalcitrant cells has been made possible through the development of retroviral vectors for delivery of both components of the system in either a single or combination of two separate viruses (Bohl et al., 1997; Hofmann et al., 1996; Kringstein et al., 1998; Paulus et al., 1996; Rossi et al., 1998). Several promoters have been used to enable generalized or tissue specific expression of tTA in plants (Weinmann et al., 1994) or animals (Efrat et al., 1995; Fishman et al., 1994; Furth et al., 1994; Hennighausen et al., 1995). Modification of the Tc-operator containing plasmid to reduce leaky expression or reduce the effects of integration site has been attempted. Strategies toward this end include Epstein Barr virus (EBV) replication origin based vectors that are maintained episomally (Jost et al., 1997), modified basal promoters to reduce uninduced expression (Hoffmann et al., 1997) and incorporation of sequences that prevent interference from adjoining elements at the site of integration (Hennighausen et al., 1995; McKnight et al., 1992; Stief et al., 1989).

The original report and several other studies have documented potential pitfalls and have provided troubleshooting strategies using the Tc regulated system (reviewed in Blau and Rossi, 1999; Gossen et al., 1994; Shockett and Schatz, 1996)). However, anecdotal evidence non-rigorously documenting failure to establish cell lines that show any significant levels of expression or inducibility of the exogenously introduced gene (Ackland-Berglund and Leib, 1995; Gossen and Bujard, 1995) exists. Drawing upon previous experiences using expression constructs with strong viral promoters based on CMV or SV-40 derived sequences, extinction of expression of transactivator function could be a potentially significant factor encountered in the inability to establish Tc-responsive cell lines. This might be of special relevance in cells having a relatively slow growth rate and/or the potential to differentiate, making them particularly sensitive to this phenomenon, since changes in cell physiology could affect the activity of exogenously introduced viral promoter constructs. The time lapsed between establishing the initial TA expressing clone and identification of cell lines inducibly expressing the gene of interest, is of a sufficient duration, during which the host cell possibly stops supporting CMV promoter enhancer expression, resulting in the shutdown of TA expression. Despite the recent introduction of retroviral vectors that enable single step and therefore relatively quick selection of positive clones, several of these also depend on viral promoters for expression of one or more elements and are therefore also prone to similar problems. The construction of a specific retrovirus is in itself time consuming and a not as yet routine procedure in many laboratories, compared to transfection or electroporation of plasmid DNA into cells. Based on these factors modification of the existing construct for rtTA cDNA expression was done by placing it under the regulation of the human Protein Translation Peptide Elongation Factor-1 α promoter (EF-1α). This gene has a housekeeping function in all cells and has been documented to be expressed to relatively high levels. More importantly, due to its indispensable housekeeping function in all cells, Protein Translation Peptide Elongation Factor-1 α promoter (EF-1α) expression is consistent from a temporal viewpoint, relatively insulated from changes in cell physiology and is cell type independent (Goldman et al., 1996; Kim et al., 1990; Wakabayashi-Ito and Nagata, 1994). Utilization of this construct in cells lines derived from diverse human tissues enabled the successful construction of Tc-regulatable lines in every case attempted so far. This modified vector will not only be of general utility but will be especially useful in cases where difficulties have been previously experienced in successfully establishing Tc-responsive clones.

SUMMARY OF THE INVENTION

The present invention provides a cell comprising the vector set forth above. The present invention further provides that the cell is from a cell line. The present invention further provides that the cell line is HeLa (human cervix), HO-1 (human melanoma), MCF-7(human breast), PC3 (human prostate) or DU-145 (human prostate).

The Invention also provides an animal comprising the vector set forth above. This invention also provides an animal which comprises a cell which comprises Protein Translation Peptide Elongation Factor-1 α promoter and nucleic acids encoding reverse tetracycline controlled transactivator, wherein the expression of said transactivator is under the control of Protein Translation Peptide Elongation Factor-1 α promoter. This invention also provides the animal includes but is not limited to a mouse.

The present invention provides a method of generating a reverse tetracycline controlled transactivator expression system for inducible tetracycline regulated gene expression comprising: (a) isolation of a DNA fragment encoding the reverse tetracycline controlled transactivator by restriction enzyme digestion (b) generation of Protein Translation Peptide Elongation Factor-1 α promoter vector, by restriction enzyme digestion (c) directional cloning of reverse tetracycline controlled transactivator into Protein Translation Peptide Elongation Factor-1 α promoter vector by ligation of 5' EcoRI compatible restriction enzyme overhangs (d) directional cloning of reverse tetracycline controlled transactivator into Protein Translation Peptide Elongation Factor-1 α promoter vector by Klenow fragment mediated blunt end generation of 3' Bam HI end of DNA fragment encoding the reverse tetracycline controlled transactivator and 3' Xbal end of Protein Translation Peptide Elongation Factor-1 α promoter vector and (e) blunt cloning of partially ligated fragment to produce Protein Translation Peptide Elongation Factor-1 α promoter vector expressing reverse tetracycline controlled transactivator.

This invention provides the fragment includes but is not limited to an Eco RI-BAM HI fragment, the mammalian expression vector includes but is not limited to pCDEF3, cloning is at the 5' Eco RI and 3' BAM HI of the insert and the ligation is at the 5' Eco RI site and the 3' Xbal site of pCDEF3.

This invention provides a method of screening pharmacological products using the vector. Finally, this invention provides a method for monitoring inducible gene expression in a tissue specific of generalized manner using the vector.

Figure 1:
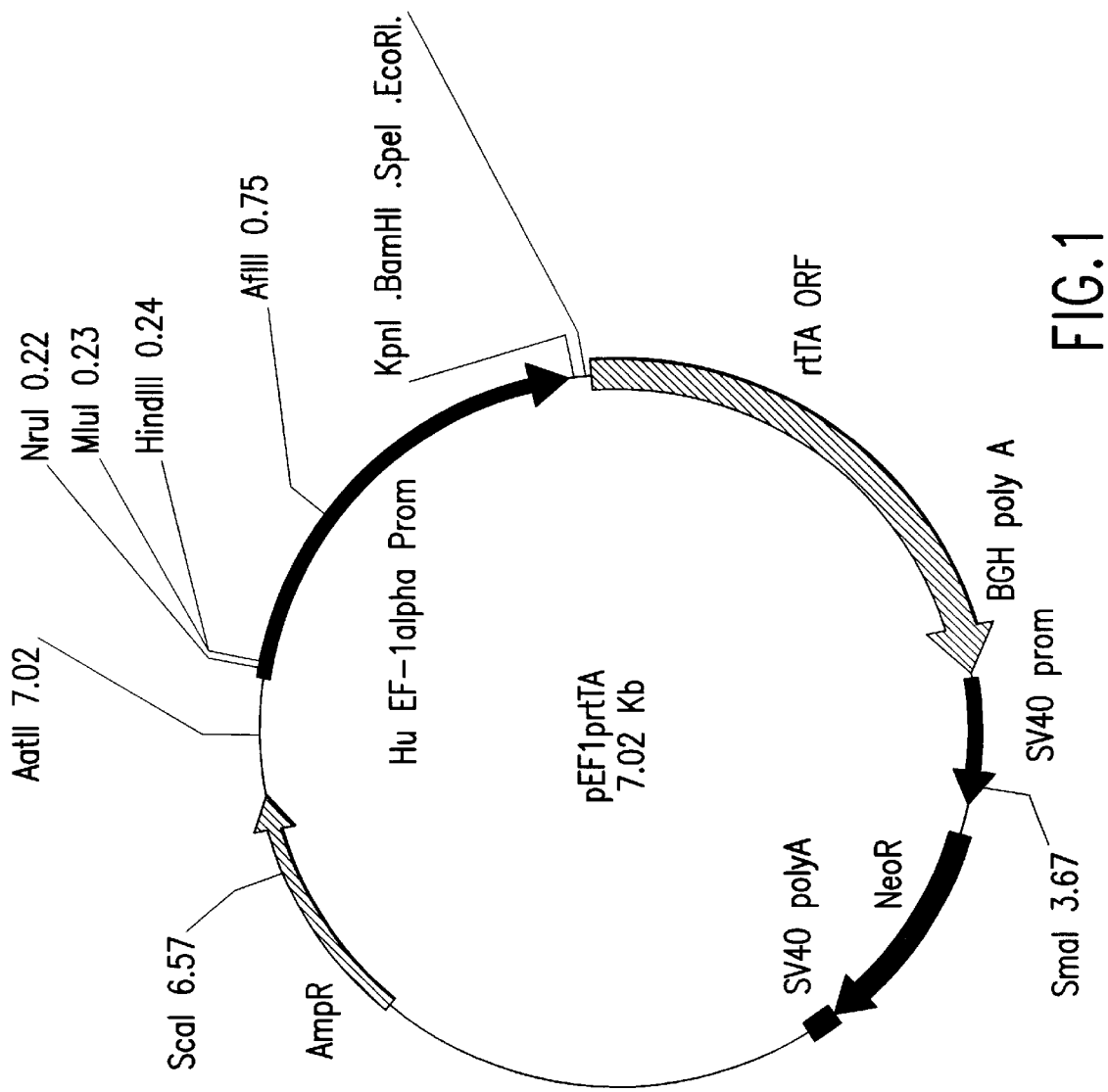
FIG. 1

Plasmid map of Protein Translation Peptide Elongation Factor-1 α expression construct: The map shows individual component elements of the vector including the rtTA ORF, human EF-1 α promoter, Bovine growth hormone (BGH) polyadenylation (poly A) signal and partial multiple cloning site retained from the vector pCDEF3(Goldman et al., 1996) after cloning. The Neomycin resistance marker (NeoR) flanked by the SV40 promoter and poly A signal, Ampicillin resistance marker (AmpR) for bacterial propagation and selection and some reference restriction site are also shown.

FIG. 2

Luciferase assay to test activity of the Protein Translation Peptide Elongation Factor-1 α promoter vector: Extracts from human HO-1 melanoma cells transiently co-transfected with the original (bars marked pUHD 17-1neo) or modified (bars marked EF1p Tet on) rtTA expression vectors and the Tc luciferase reporter pUHC 13-3 were quantitated for luciferase activity. These extracts were prepared from cells treated without the inducer (−Dox) or with (+Dox). Treatment with inducer was for 48 h as described in materials and methods.

FIGS. 3A–3E

Luciferase assay to select Tc-inducible clones: Panels show quantitation of luciferase assays from individual Neomycin resistant clonally isolated cell lines of human prostate (DU-145 and PC3), cervical (HeLa), breast (MCF-7) and melanoma (HO-1) tumor origin. Each stable clone was transiently transfected with the Tc luciferase reporter pUHC 13-3 in the absence (−Dox) or presence (+Dox) of inducer. Extracts prepared from these cells were assayed for luciferase activity to identify clones showing adequate levels of inducibility for each cell type as described in material and methods.

FIGS. 4A–4B

Northern blot analysis of individual Tc responsive clones expressing regulatable Mda-7 or Jun B cDNAs: Autoradiographic detection of levels of induced RNA message levels expressed in clonally selected cells stably transfected with the Mda-7 (A) or Jun B (B) cDNAs under regulation of Tc, probed with respective radiolabelled cDNA probes after transfer to nylon membranes. Each similarly numbered sample was derived from the same clone without induction [1-17 (A) and 1-9 (B) or after addition of inducer, 1'-17' (A) and 1'-9' (B)].

DETAILED DESCRIPTION OF THE INVENTION

The present invention provides a vector comprising an Protein Translation Peptide Elongation Factor-1 α promoter and nucleic acids encoding reverse tetracycline controlled transactivator, wherein the expression of said transactivator is under the control of Protein Translation Peptide Elongation Factor-1 α promoter. In an embodiment the vector is a plasmid. In another embodiment the vector is as set forth in FIG. 1.

The present invention further provides a cell comprising the vector set forth above. In an embodiment the cell is from a cell line. In a further embodiment the cell line is HeLa (human cervix), HO-1 (human melanoma), MCF7 (human breast), PC3 (human prostate) or DU-145 (human prostate).

The invention also provides an animal comprising the vector set forth above. An embodiment of this invention the vector has been introduced into the animal or an ancestor of the animal at an embryonic stage. The animal includes but is not limited to a mouse.

This invention also provides an animal which comprises a cell which comprises Protein Translation Peptide Elongation Factor-1 α promoter and nucleic acids encoding reverse tetracycline controlled transactivator, wherein the expression of said transactivator is under the control of Protein Translation Peptide Elongation Factor-1 α promoter.

The present invention provides a method of generating a A method of generating a reverse tetracycline controlled transactivator expression system for inducible tetracycline regulated gene expression comprising: (a) isolation of a DNA fragment encoding the reverse tetracycline controlled transactivator by restriction enzyme digestion (b) generation of Protein Translation Peptide Elongation Factor-1 α promoter vector, by restriction enzyme digestion (c) directional cloning of reverse tetracycline controlled transactivator into Protein Translation Peptide Elongation Factor-1 α promoter vector by ligation of 5' EcoRI compatible restriction enzyme overhangs (d) directional cloning of reverse tetracycline controlled transactivator into Protein Translation Peptide Elongation Factor-1 α promoter vector by Klenow fragment mediated blunt end generation of 3' Bam HI end of DNA fragment encoding the reverse tetracycline controlled transactivator and 3' XbaI end of Protein Translation Peptide Elongation Factor-1 α promoter vector and (e) blunt cloning of partially ligated fragment to produce Protein Translation Peptide Elongation Factor-1 α promoter vector expressing reverse tetracycline controlled transactivator.

In accordance with the method of the invention, the fragment includes but is not limited to an Eco RI-BAM HI fragment, the mammalian expression vector includes but is not limited to pCDEF3, cloning is at the 5' Eco RI and 3' BAM HI of the inserts and the ligation is at the 5' Eco RI site and the 3' Xbal site of pCDEF3.

The present invention provides a vector which is directed to providing a consistent cellular expression of the tetracycline repressor in cells. Such a vector may be useful in situations requiring inducible gene expression in a tissue specific or generalized manner in animal or plant models. In one embodiment of the invention, pharmacological products are monitored to determine use in medical applications. In the preferred embodiment monitoring is of she gene changes associated with cellular process such as aging, cancer, development, differentiation and growth.

More specifically, methods which are well known to those skilled in the art can be used to construct a vector directed to providing a cellular expression of the tetracycline repressor in cells. These methods include in cell culture techniques, northern blotting, enzyme activity analysis, construction of plasmids and sequencing. See e.g., the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

As used herein the term "tetracycline controlled transactivator" encompasses a vector expressing a protein that binds and activates transcription of downstream tetracycline induced operator binding elements, only when tetracycline is present.

This invention provides a method of screening pharmacological products using the vector. Finally, this invention provides a method for monitoring inducible gene expression using the vector.

This invention is illustrated in the Experimental Details section which follows. This section is set forth to aid in understanding the invention but is not intended to, and should not be construed to, limit in any way the invention as set forth in the claims which follow thereafter.

EXPERIMENTAL DETAILS

Materials and Methods

Construction of Plasmids:

An Eco RI-Bam HI fragment containing the rtTA open reading frame was isolated from pHUD 17-1neo (Gossen et al., 1995). This fragment was cloned directionally into the mammalian expression vector pCDEF3 (Goldman et al., 1996) at the 5' Eco RI and 3' Xba sites of the vector multiple cloning site to generate the final construct termed, EF1prtTA. Ligation of the 3' Xba I site of pCDEF3 and the BamHI site of the fragment was possible after Klenow filling the overhangs to make them blunt-ended. This modified vector places the rtTA gene under direct transcriptional control of the human polypeptide chain elongation factor-1alpha promoter (EF-1α). Plasmids expressing the Mda-7 and Jun B cDNAs were constructed in pUHD 10-3 (Gossen and Bujard, 1992) by blunt cloning of isolated cDNA fragments into Klenow filled blunt vector followed by sequence analysis for confirmation.

Cell Culture and Derivation of Stable Cell Lines:

All cell lines used in this study were grown and maintained under standard conditions as previously described (Giang et al., 1996). Selection of stable clones expressing the rtTA cDNA using EF1prtTA was carried out in the presence of 500 to 1000 μg/ml G148 (Life Technologies Inc.) depending on the individual cell line. After the selection period, macroscopic visible colonies were picked, expanded and analyzed for activity by assaying for luciferase activity for rtTA expression or by Northern blot analysis of inducible cDNA such as Mda-7 or Jun B respectively.

Northern Blotting:

Total cellular RNA was resolved by denaturing formaldehyde agarose gel electrophoresis after isolation of RNA using an RNAeasy Kit (Qiagen). Transfer was done onto Hybond nylon membranes (Amersham) and probed with appropriately labeled cDNA probes for Mda-7 and Jun B.

Luciferase Activity Analysis:

Luciferase assays were performed using a Luciferase Assay Kit (Promega) and quantitation was performed on a Turner Design TD 20/20 luminometer. Equal quantities of RNA were loaded on each gel following spectrophotometric estimation at 260 nm. Normalization of RNA levels between samples was confirmed by visualizing RNA on ethidium bromide stained gels. Normalization of luciferase activity was achieved by quantitating protein and adjusting the amount of extract to a fixed amount of protein.

RESULTS

Figure 2:
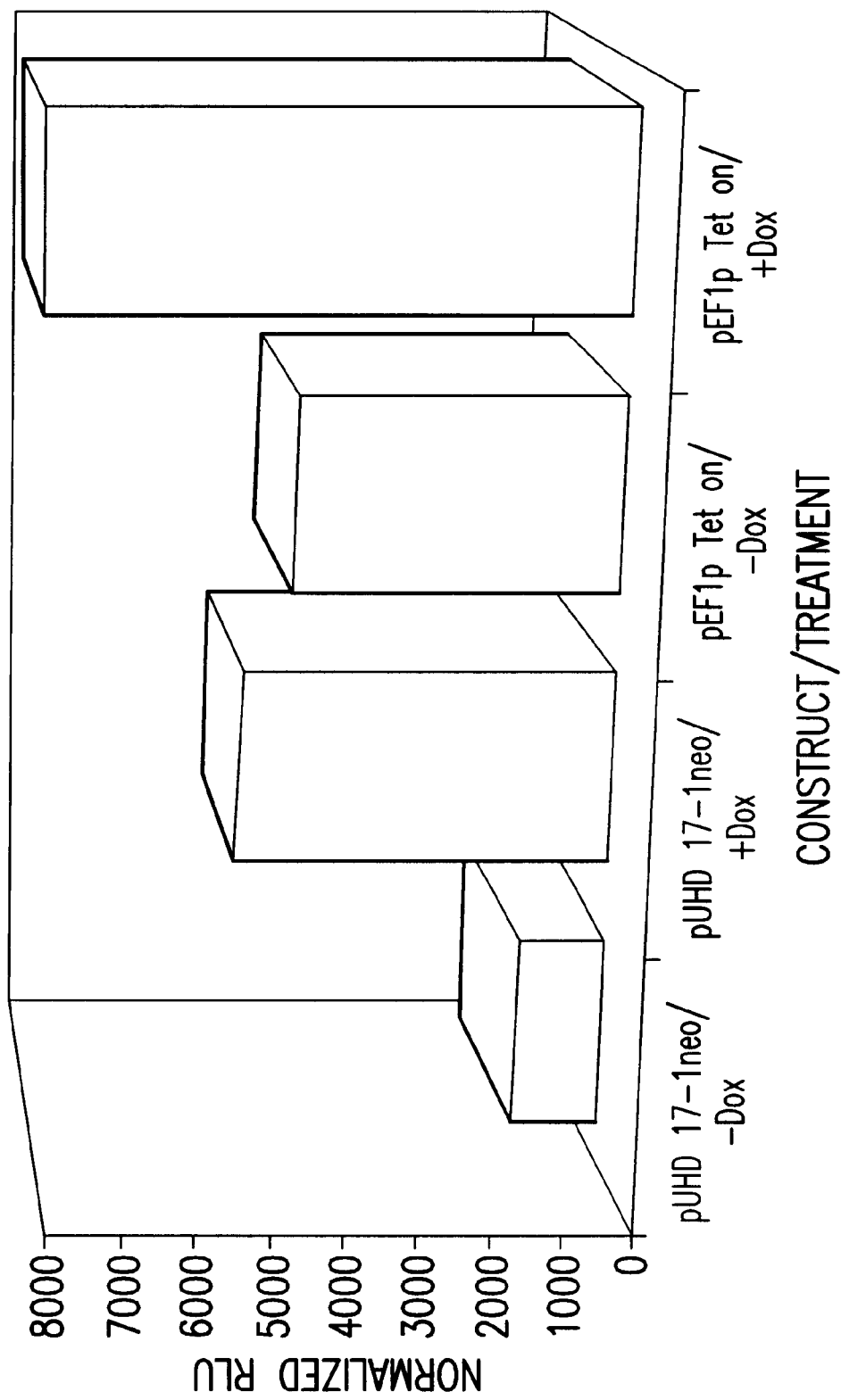

Construction and Initial Testing of the EF-1a Promoter Based rtTA Expression Vector Details of the cloning steps performed in construction of the EF-1 a promoter rtTA (EF1prtTA) expression vector is described in materials and methods and FIG. 1. The protein expressed by this cDNA, a mutant form of the original bacterial Tc-repressor (Gossen et al., 1995), binds to and activates transcription of genes downstream of Tc-operator binding elements, only when Tc is present. EF1prtTA was transiently co-transfected with the Tc-responsive luciferase reporter plasmid, pUHC 13-3 (Gossen et al., 1995), into HO-1 human melanoma cells to determine if the construct was active. A parallel set of transfections was performed with the original CMV IE based construct, pUHD 17-1neo (Gossen et al., 1995) in the absence or presence of 1 μg/ml doxycycline (Dox). Cells were harvested 48 h after transfection and luciferase activity (FIG. 2) was determined using a luminometric Luciferase assay system (Promega). As previously documented (Gossen et al., 1994; Gossen and Bujard, 1992; Gossen et al., 1995) transient assays poorly reflect the level of inducibility actually obtainable after final selection of stable clones, since basal levels of expression change dramatically once plasmid DNA is integrated into chromatin. The initial experiments clearly demonstrated that the EF1prtTA expression vector was functional at comparable levels to the original pUHD 17-1neo construct in transient assays. Based on the positive activity obtained, the EF1prtTA construct was utilized to establish stable lines expressing rtTA in HeLa (human cervical carcinoma), HO-1, (human melanoma) MCF-7 (human breast carcinoma) and PC3 and DU-145 (human prostate carcinoma) cancer cell lines.

Analysis of Stable Cell Lines Expressing the rtTA cDNA Under Regulation of the EF-1α Promoter Cells were transfected with the EF1prtTA construct using Superfect transfection reagent (Qiagen) based on standard conditions recommended in the usage protocol. The efficiency of transfection, reflected by the number of clones obtained at the end of the selection period, varied with each cell line. Colonies were selected using Neomycin resistance conferred by the marker present within the construct. For every cell line, twenty-four Neomycin resistant colonies were isolated for further analysis. These individually selected clones were transiently transfected with the Tc-responsive luciferase reporter pUHC 13-3 (Gossen et al., 1995) to determine the presence and level of rtTA activity. Some cell lines used in this series of experiments had failed to generate Tc-responsive clones in previous attempts utilizing the CMV IE based construct pUHD 17-1neo (Gossen et al., 1995).

Figure 3D:
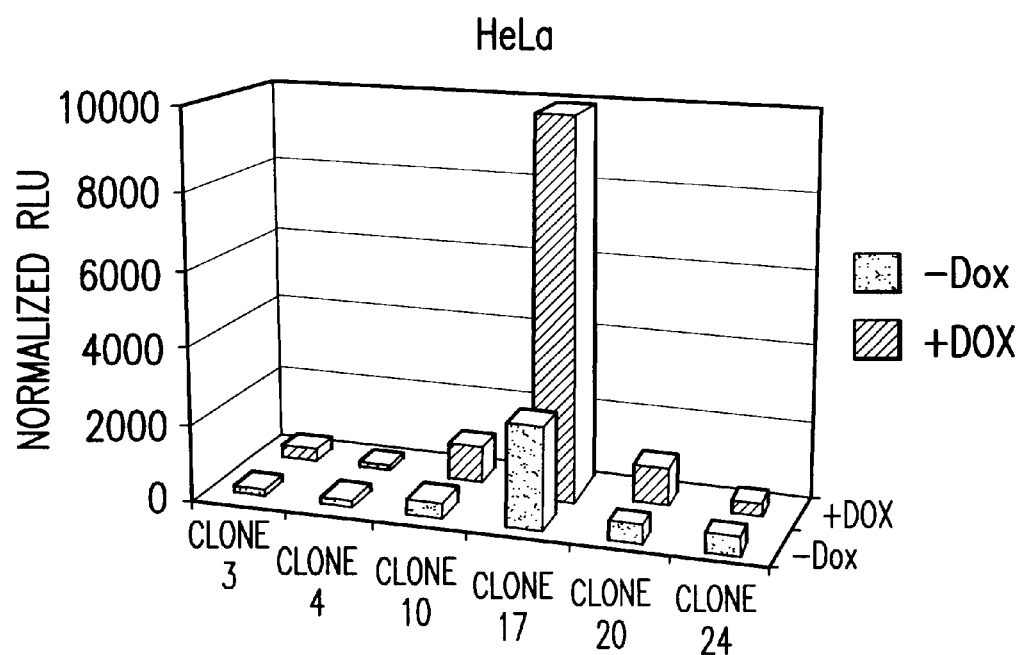
Figure 3E:
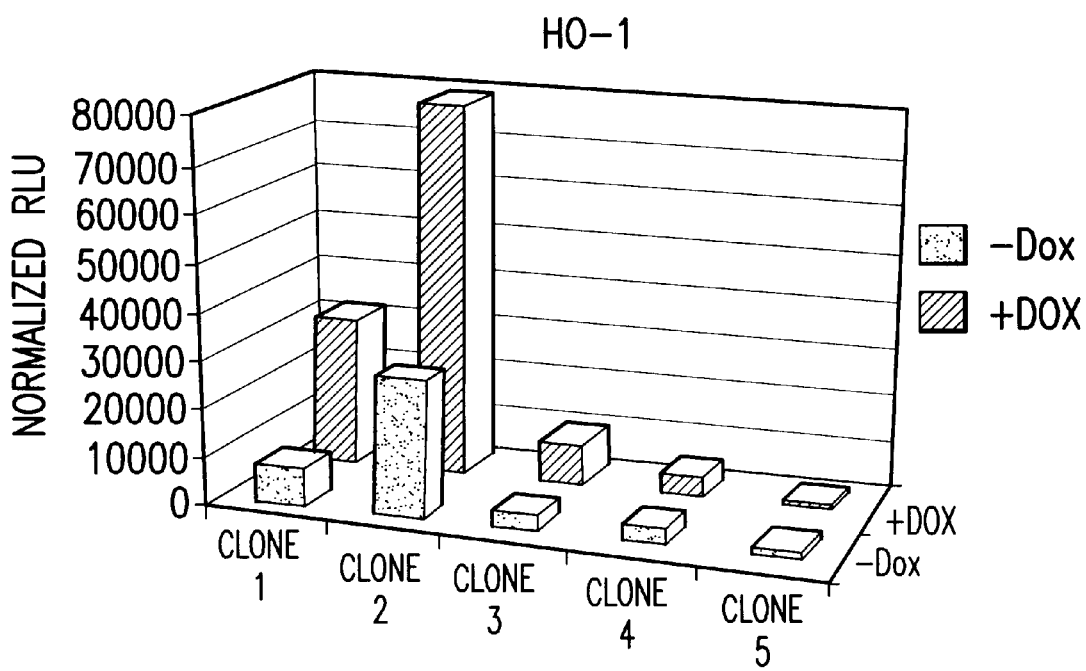

Results obtained in a screen to identify Tc-responsive clonal cell lines in HO-1, MCF-7, PC3 and DU-145 cells (FIG. 3) indicated that an average of at least two clones of the twenty-four or less clones finally analyzed per cell line, showed some levels of Tc-responsiveness. This frequency of positive clones is comparable, if not higher than that reported previously (Gossen and Bujard, 1992; Gossen et al., 1995). As mentioned above, the fold induction observed in the presence of Tc, though relatively low, is likely to be a reflection of leaky expression in uninduced conditions due to the transient transfection conditions used in this initial screen. Despite this leakyness, clones with high or low relative levels of inducibility were identifiable in every case and potentially usable cell lines were identified with relative ease.

Figure 4A:
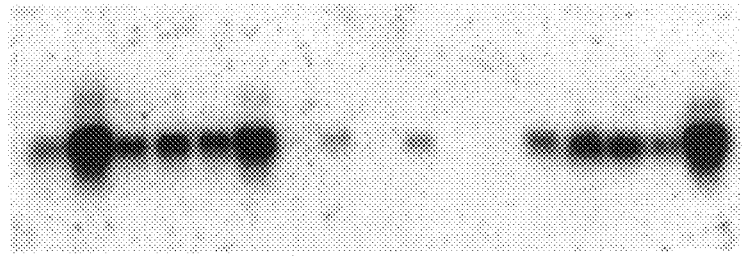
Figure 4A:
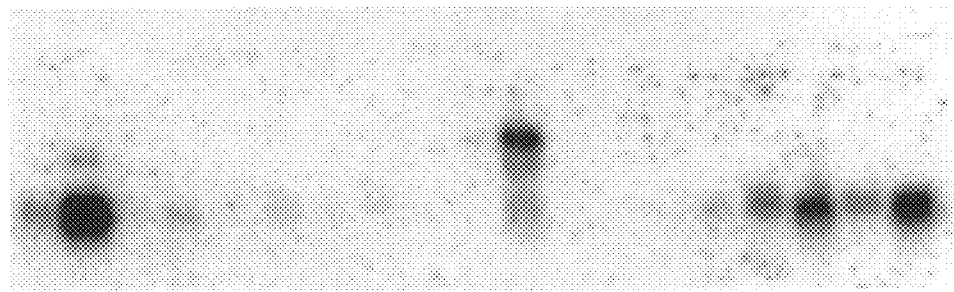
Figure 4B:
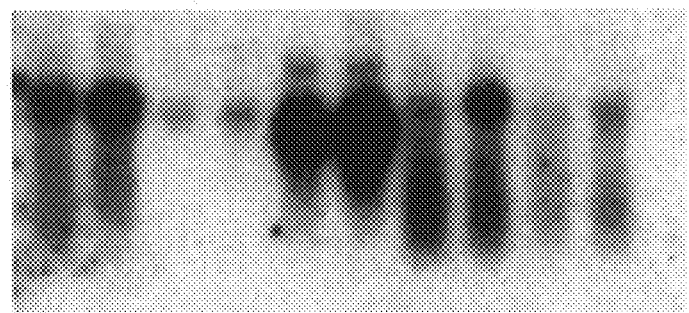
Figure 4B:
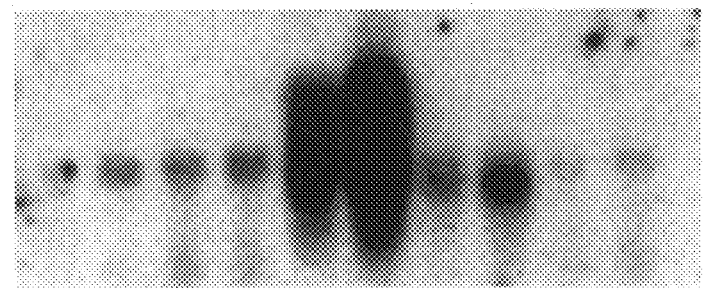

Functional Analysis of Stable Clones Expressing cDNAs Under Inducible Regulation of EF1prtTA In continuance of a major focus of our research involving analysis of the role of specific genes in melanoma differentiation, stable cells expressing differentiation associated genes including the transcription factor Jun B and the tumor suppressor Mda-7 (Jiang et al., 1996) under Tc-regulation were established in HO-1 melanoma cells. This human melanoma cell line has the ability to terminally differentiate in the combined presence of β-interferon and the Protein Kinase C (PKC) activator, mezerein. It is sensitive to culture conditions due to its capacity to differentiate, difficult to transfect and takes a relatively long time during selection to form visible colonies suitable for re-isolation as a clonal population of cells. HO-1 therefore presents an ideal proving ground for the efficacy of the EF-1 α promoter based vector. Using a suitable rtTA expressing cell line identified in the previous screen described above (FIG. 3), transfections were performed with the potentially Tc-regulatable Jun B and Mda-7 cDNAs cloned into the vector pUHD 10-3 (Gossen and Bujard, 1992). Colonies were isolated and individual clones were analyzed for expression and induction of Jun B and Mda-7 by Northern blotting. To determine the level of inducibility of individual clones, RNAs were isolated from each clone grown in the absence or presence of Dox. Northern blots, probed with Jun B and Mda-7 cDNA probes (FIG. 4) indicated that several positive clones had been obtained for each cDNA. As anticipated, varying degrees of clone dependent basal and inducible levels of expression was observed. It may be noted that the parental EF1prtTA cell line chosen from the initial screen (previous section, FIG. 3) had not exhibited a very high level of fold inducibility in transient assays. However, on introduction of a Tc-operator regulatable construct, in a stably integrated form, high levels of Tc-dependent induction was observed in individual clones (FIG. 4A compare lanes 1, 3, 9, 10 and 17, induced and uninduced level and similarly FIG. 4B lanes 1, 4 and 9). Overall, the frequency, variability and basal to induced levels obtained in various clones closely parallels that reported for the Tc-system (Gossen et al., 1994; Gossen and Bujard, 1992; Gossen et al., 1995).

DISCUSSION

Inability to support continual strong expression from a given type of promoter, specifically those of viral origin has been documented for certain cell types (Gorman et al., 1985; Hasegawa et al., 1990 Li et al., 1992; Miller and Rizzino, 1995; Sleigh, 1987). The primary goal of this work is to reduce a significant and hitherto unaddressed variable in successfully establishing Tc-inducible cells. Expression of the Tc-operator expression construct, pUHD 10-3 (Gossen and Bujard, 1992) or its derivatives, into which the cDNA of interest is usually cloned, is ultimately dependent on expression of the tTA or rtTA gene product. Preventing or avoiding TA cDNA expression is shut down, during or subsequent to establishing a cell line, a variable that is likely to be cell type associated (Ackland-Berglund and Leib, 1995; Gossen and Bujard, 1995) should considerably enhance success rates. To achieve steady and adequate levels of the TA cDNA expression, relatively independent of temporal factors, cell-type, cell physiology status and cell passage number, we replaced the CMV IE promoter enhancer with the cellular EF-1 α promoter (Goldman et al., 1996; Kim et al., 1990; Wakabayashi-Ito and Nagata, 1994). Experience in using pUHD 17-1neo (Gossen et al., 1995) indicated that while activity and inducibility in transient assays using sensitive detection methods with luciferase reporters worked reasonably well, we failed to generate cells stowing any level of activity of the gene of interest after clonal selection of individual lines, despite presence of expression construct DNA, in the genome using Southern analysis (data not shown).

Numerous modifications of the basic Tc-regulatable system have been reported in the literature directed toward enhancing performance. Several alternative promoters have been utilized to drive expression of the TA cDNA. Many of these are based on the requirement for tissue or species specific expression in plants (Weinmann et al., 1994), Drosophila (Bieschke et al., 1998) or mice, (Bohl et al., 1997; Dhawan et al., 1995; Faiss et al., 1997; Hennighausen et al., 1995; Hoffmann et al., 1997; Holwell et al., 1997; Li et al., 1992; Liang et al., 1996; Miller and Rizzino, 1995; Thompson and Myatt, 1997). Another modification of the TA expressing construct involves use of bi- or multi-cistronic plasmid constructs which drives expression, through oppositely oriented promoters, of both TA-cDNA and Tc-operator regulated cDNAs, mainly to circumvent two rounds of transfection of separate plasmids (Baron et al., 1995 Fussenegger et al., 1997; Liang et al., 1996; Schultze et al., 1996; Weinmann et al., 1994). However they are based on one or a combination of viral promoters with accompanying drawbacks mentioned above. Multi-cistronic single retroviral or combinations of two or more retroviruses expressing different components has also been constructed (Bohl et al., 1997; Hofmann et al., 1996; Kringstein et al., 1998; Paulus et al., 1996; Rossi et al., 1998). These overcome the barrier of gene delivery into cells but again expression is often based on viral promoter sequences, prone to possible shutdown in some cell types. The relatively complex steps involved in making a virus for a given cDNA of interest including the intricate cloning strategies due to large vector size and investment in time, somewhat offsets the advantages they present over classical DNA transfection approaches. Making retroviral vectors is presently restricted to a relatively small proportion of laboratories and safety concerns impose limitations of use in several setups. Therefore, while these vectors hold considerable promise, the likelihood of a major shift over to their usage from widespread DNA transfection approaches may only be in the long term. The relevance of improved plasmid vectors is therefore still strong.

A generally applicable modification to the original TA-expression construct involved expression of both TA-cDNA and exogenous cDNA under regulation of Tc-operator sequences (Liang et al., 1996; Shockett et al., 1995). The rationale being that, exquisite regulation with very high inducibility could be built into a system when both the activator molecule and the regulatable gene of interest are under control of the same inducer through an autoregulatory loop. Unfortunately, it appears that the high levels of tTA protein produced as a result of induction results in toxic, side effects in cells (Gallia and Khalili, 1998; Gossen and Bujard, 1992) most likely due to interference in cellular metabolism by the acid activation domain of the HSV, VP16 protein present in TA-proteins. This could be an additional reason why certain cell types apparently shut down expression of TA-cDNA after extended periods time. Alternatively, cells strongly expressing TA proteins might be at a selective disadvantage, particularly in cells with a long doubling time due to accumulation of toxic levels of TA protein. While we can only speculate about the true reason for the apparent loss of TA expression, it appears that switching over to the EF-1 α expression cassette is able to balance out and over come these problems.

The conclusion is based on observations over periods of time, extending to almost twelve months in the case of certain EF1prtTA cells lines such as those established in a HO-1 melanoma. The parental HO-1 EF1prtTA cell line was made and initially analyzed over a period of time (>60 days) before being expanded and frozen for future use. These parental cells were used to establish inducible Jun B and Mda-7 expression (FIG. 4, A and B) that showed functional levels of TA-expression and inducible properties after being thawed out several months and passage numbers subsequent to when the line had initially been established and frozen. This line and others (FIG. 3) continue to retain Tc-responsive properties and were all maintained in the absence of antibiotic selection, indicating that expression of the rtTA cDNA continued irrespective of lack of positive selective pressure, passage number and time elapsed between introduction and integration of the plasmid DNA and final usage. Overall, following modification of the expression construct for the rtTA cDNA we have demonstrated that it had enabled us to significantly enhance the likelihood of establishing cell lines that are Tc-regulatable. It appeared that positive clones were obtained at higher frequencies than previously reported and that consistent expressions and clonal stability over an extended period of time was accomplished. Based on these observations we conclude that the modified EF1prtTA presents a useful reagent with broad applicability in establishing Tc-regulatable cells.

REFERENCES

1. Ackland-Berglund, C. E., and Leib, D. A., (1995) "The Efficacy of Tetracycline-Controlled Gene Expression is Influenced by Cell Type" Bio. Techniques 18:196–200;
2. Baron, U., Ferundlieb, S., Gossen, M., and Bujard, H., (1995) "Co-regulation of two gene activities by tetracycline via a bidirectional promoter" Nuc. Acd. Res., 23:3605–3606;
3. Bieschke, E. E., Wheeler, J. C., and Tower, J., (1998) "Doxycycline-induced transgene expression during Drosophilia development and aging" Mol. Gen. Genet., 258:571–579;
4. Blau, H., and Rossi, F. M. V., (1999) "Tet B or not tet B: Advances in tetracycline-inducible gene expression" Proc. Natl. Acad. Sci. USA, 96:797–799;
5. Bohl, D., Naffakh, N., and Heard, J. M., (1997) "Long-term control of erythoropoietein secretion by doxycycline in mice transplanted with engineered primary myoblasts" Nat. Med., 3:299–305;
6. Dhawan, J., Rando, T. A., Elson, S. L., Bujard, h., and Blau, H. M., (1995) "Tetracycline-regulated gene expression following direct gene transfer into mouse skeletal muscle" Somat. Cell. Mol. Genet., 21:233–240;
   Efrat, S., Fusco-DeMane, D., Lemberg, H., al Emran, O., and Wang, X., (1995) "Conditional transformation of a pancreatic beta-cell line derived from transgenic mice expressing a tetracycline-regulated oncogene" Proc. Natl. Acad. Sci USA, 92:3576–3580;
7. Faiss, M., Zalubilova, J., Strnad, M., and Schmulling, T., (1997) "Conditional transgenic expression of the ipt gene indicates a function for cytokinins in paracrine signaling in whole tobacco plants" Plant J., 12:401–415;
8. Fishman, G. I., Kaplan, M. L., and Buttrick, P. M., (1994) "Tetracycline-regulated cardiac gene expression in vivo" J. Clin. Invest., 93:1864–1868;
9. Furth, P. A., St Onge, L., Boger, H., Gruss, P., Gossen, M., Kistner, A., Bujard, H., and Hennighausen, L., (1994) "Temporal control of gene expression in transgenic mice by a tetracycline-responsive promoter" Proc. Natl. Acad. Sci USA, 91:9302–9306;
10. Fussenegger, M., Moser, s., Mazur, X., and Bailey, J. E., (2997) "Autoregulated multicistronic expression vectors provide one-step cloning of regulated product gene expression in mammalian cells" Biotrechnol Prog., 13:733–740;
11. Gallia, G. L., and Khalili, K., (1998) "Evaluation of an autoregulatory tetracycline regulated system" Oncogene, 16:1879–18884;
12. Goldman, L. A., Cutrone, E. C., Kotenko, S. V., Krause, C. D., and Langer, J. A., (1996) "Modifications of vectors pEF-BOS, pcDNA1 AND pcDNA3 result in improved convenience and expression" BioTechniques, 21:1013–1015;
14. Gorman, C. M., Rigby, P. W., and Lane, D. P., (1985) "Negative regulation of viral enhancers in undifferentiated embryonic stem cells" Cell, 42:519–526;
15. Gossen, M., Bonin, A. L., Freundlieb, S., and Bujard, H., (1994) "Inducible gene expression systems for higher eukaryotic cells" Curr. Opin. Biotechnol, 5:516–520;

16. Gossen, M., and Bujard, H., (1995) "Efficacy of tetracycline-controlled gene expression influenced by cell type: commentary" *Biotechniques*, 19:213–216;
17. Gossen, M., and Bujard, H., (1992) "Tight control of gene expression in mammalian cells by tetracycline-responsive promoters" *Proc. Natl. Acad. Sci. USA*, 89:5547–5551;
18. Gossen, M., Freundlieb, S., Bender, G., Muller, G., Hillen, W., and Bujard, H., (1995) "Transcriptional activation by tetracyclines in mammalian cells" *Sci.*, 268:1766–1769;
19. Hasegawa, T., Nakada, S., Nakajima, T., Oda, K., Kawata, M., Kimura, H., and Sekiya, S., (1990) "Expression of various viral and cellular enhancer-promoters during differentiation of human embryonal carcinoma cells" *Diff.*, 42:191–198;
20. Hennighausen, L., Wali, R. J., Tillmann, U., Li, M., and
21. Furth, P. A., (1995) "Conditional gene expression in secretory tissues and skin of transgenic mice using the MMTV-LTR and the tetracycline responsive system" *J. Cell. Biochem.*, 59:463–472;
22. Hoffmann, A., Villalba, M., Journot, L., and Spengler, D., (1997) "A novel tetracycline-dependent expression vector with low basal expression and potent regulatory properties in various mammalian cell lines" *Nucl. Acd. Res.*, 25:1078–1079;
23. Hoffmann, A., Nolan, G. P., and Blau, H. M., (1996) "Rapid retroviral delivery of tetracycline-inducible genes in a single autoregulatory cassette" *Proc. Natl. Acad. Sci. USA*, 93:5185–5190;
24. Holwell, T. A., Schweitzer, S. C., and Evans, R. M. (1997) "Tetracycline regulated expression of vimentin in fibroblasts derived from vimentin null mice" *J. Cell. Sci.*, 110:1947–1957;
25. Jiang, H., Su, Z. Z., Lin, J. J., Goldstein, N. I., Young, C. S., and Fisher, P. B. (1996) "The melanoma differentiation associated gene mda-7 suppresses cancer cell growth" *Proc. Nati. Acad. Sci. USA*, 93:9160–9165;
26. Jost, M., Kari, C., and Rodeck, U., (1997) "An episomal vector for stable tetracycline-regulated gene expression" *Nucl. Acds. Res.*, 25:3131–3134;
27. Kang, D. C., Motwani, M., and Fisher, P. B., (1998) "Role of the transcription factor AP-1 in melanoma differentiation (review)" *Int. J. Oncol.*, 13:1117–1126;
28. Kim, D. W., Uetsuki, T., Kaziro, Y., Yamaguchi, N., and Sugano, S., (1990) "Uses of the human elongation factor 1 alpha promoter as a versatile and efficient expression system" *Gene*, 91:217–223;
29. Kringstein, A. M., Rossi, F. M., Hofmann, A., and Blau, H. M., (1998) "Graded transcriptional response to different concentrations of a single trasactivator" *Proc. Natl. Acad. Sci. USA*, 95:13670–13675;
30. Li, M., Hantzopoulos, P. A., Banerjee, D., Zhao, S. C., Schweitzer, B. I., Gilboa, E., and Bertino, J. R., (1992) "Comparison of the expression of a mutant dihydrofolate reductase under control of different internal promoters in retroviral vectors" *Hum. Gene Ther.*, 3:381–390;
31. Liang, X., Hartikka, J., Sukhu, L., Manthorpe, M., and Hobart, P., (1996) "Novel, high expressing and antibiotic-controlled plasmid vectors designed for use in gene therapy" *Gene Tehr.*, 3:350–356;
32. McKnight, R. A., Shamay, A., Sankaran, L., Wall, R. J., and Hennighausen, L. (1992) "Matrix-attachment regions can impart position-independent regulation of a tissue-specific gene in transgenic mice" *Proc. Natl. Acad. Sci. USA*, 89:6943–6947;
33. Miller, K., and Rizzino, A., (1995) "The function of inducible promoter systems in F9 embryonal carcinoma cells" *Exp. Cell Res.*, 218:144–150;
34. Paulus, W., Baur, I., Boyce, F. M., Breakefield, X. O., and Reeves, S. A., (1996) "Self-contained, tetracycline-regulated retroviral vector system for gene delivery to mammalian cells" *J. Virol*, 70:62–67;
35. Rossi, F. M., Guicherit, O. M., Spicher, A., Kringstein, A. M., Fatyol, K., Blakely, B. T., and Blau, H. M., (1998) "Tetracycline-regulatable factors with distinct dimerization domains allow reversible growth inhibition by p16." *Nat. Genet.*, 20:389–393;
36. Schultze, N., Burki, Y., Lang, Y., Certa, U., and Bluethmann, H., (1996) "Efficient control of gene expression by single step integration of the tetracycline system intransgenic mice" *Nat. Biotechnol.*, 14:499–503;
37. Shockett, P., Difilippantonio, M., Hellman, N., and Schatz, D. G., (1995) "A modified tetracycline-regulated inducible gene expression" *Proc. Natl. Acad. Sci. USA*, 92:6522–6566;
38. Shockett, P. E., and Schatz, D. G., (1996) "Diverse strategies for tetracycline-regulated inducible gene expression" *Proc. Natl. Acad. Sci. USA*, 93:5173–5176;
39. Sleigh, M. J., (1987) "Differential regulation of viral and cellular genes in F9 mouse embryonal carcinoma cells" *Nucl. Acds. Res.*, 15:9379–9395;
40. Stief, A., Winter, D. M., Stratling, W. H., and Sippel, A. E., (1989) "A nuclear DNA attachment element mediates elevated and position-independent gene activity" *Nature*, 341:343–345;
41. Thompson, A. J., and Myatt, S. C., (1997) "Tetracycline-dependent activation of an upstream promoter reveals transcriptional interference between tandem genes within T-DNA in tomato" *Plant Mol. Biol.*, 34:687–692;
42. Wakabayashi, N., and Nagata, S., (1994) "Characterization of the regulatory elements in the promoter of the human elongation factor-1 alpha gene" *J. Biol. Chem.*, 269:29831–29837; and
43. Weinmann, P., Gossen, M., Hillen, W., Bujard, H., and Gatz, C., (1994) "A chimeric transactivator allows tetracycline-responsive gene expression in whole plants" *Plant J.*, 5:559–569.

What is claimed is:

1. A vector comprising:
   a) a first promoter comprising a human Protein Translation Peptide Elongation Factor-1α promoter;
   b) a nucleic acid encoding a tetracycline controlled transactivator, wherein the nucleic acid encoding said transactivator is operably linked to said first promoter;
   c) a second promoter operably linked to at least one copy of a tetracycline induced operator binding element, and
   d) a gene of interest operably linked to said second promoter.
2. The vector of claim 1, wherein the vector is a plasmid.
3. The vector of claim 1, wherein the vector is as set forth in FIG. 1.
4. An isolated cell comprising the vector of claim 1.
5. The cell of claim 4, wherein the cell is from a cell line.
6. The cell of claim 5, wherein the cell line is HeLa (human cervix), HO-1 (human melanoma), MCF-7 (human breast), PC3 (human prostate) or DU-145 (human prostate).
7. A method for expressing a gene of interest comprising contacting the cell of claim 4 with an inducer of the tetracycline induced operator binding element so as to cause the cell to express the gene of interest.
8. The method of claim 7, wherein the inducer is tetracycline or doxycycline.

* * * * *